US005843441A

United States Patent [19]

Gundel et al.

[11] Patent Number: 5,843,441
[45] Date of Patent: Dec. 1, 1998

[54] USE OF ENDOTHELIAL-LEUKOCYTE ADHESION MOLECULE-1 SPECIFIC ANTIBODIES IN THE TREATMENT OF ASTHMA

[75] Inventors: Robert H. Gundel, Walnut Creek, Calif.; Craig D. Wegner, Mundelein, Ill.; L. Gordon Letts, Dover, Mass.; C. Wayne Smith, Sugarland, Tex.

[73] Assignee: Boehringer Ingelheim, Ridgefield, Conn.

[21] Appl. No.: 504,257

[22] Filed: Jul. 19, 1995

(Under 37 CFR 1.47)

Related U.S. Application Data

[63] Continuation of Ser. No. 166,562, Dec. 3, 1993, abandoned, which is a continuation of Ser. No. 738,633, Jul. 31, 1991, abandoned.

[51] Int. Cl.$^6$ ......................... A61K 39/395; C07K 16/28
[52] U.S. Cl. ..................................... 424/143.1; 424/152.1; 424/172.1; 530/388.2; 530/388.22
[58] Field of Search ............................. 424/130.1, 133.1, 424/141.1, 143.1, 152.1, 172.1; 530/382.1, 388.1, 388.2, 388.22

[56] References Cited

FOREIGN PATENT DOCUMENTS 387701   2/1989   European Pat. Off. .
WO 90/05539   3/1990   WIPO .

OTHER PUBLICATIONS

Harris, W.J. et al., "Therapeutic Antibodies—The Coming of Age", *TIBTECH* 11:42–44 (1993).
Mulligan, M.S. et al., "Role of Endothelial–Leukocyte Adhesion Molecule 1 (ELAM–1) in Neutrophil–mediated Lung Injury in Rats," *J. Clin. Invest.* 88:1396–1406 (1991).
Gundel, R.H. et al., "Endothelial Leukocyte Adhesion Molecule–1 Mediates Antigen–Induced Acute Airway Inflammation and Late–Phase Airway Obstruction in Monkeys," *J. Clin. Invest.* 88:1407–1411 (1991).
Bevilacqua, M.P. et al., "Endothelial Leukocyte Adhesion Molecule 1: An Inducible Receptor for Neutrophils Related to Complement Regulatory Proteins and Lectins," *Science* 243: 1160–1165 (1989).
Carlos, T.M. et al., "Membrane Proteins Involved in Phagocyte Adhesion to Endothelium," *Immunol. Rev.* 114:5–28 (1990).
Luscinskas, F.W. et al., "Endothelial–Leukocyte Adhesion Molecule–1–Dependent and Leukocyte (CD11/CD18)–DependentMechanisms Contribute To Polymorphonuclear Leukocyte Adhesion to Cytokine–Activated Human Vascular Endothelium." *J. Immunol.* 14:2257–2263 (1989).
Mendis, A.H. et al., "Study of Human Epithelial Cell Detachment and Damage: Effects of Proteases and Oxidants," *Immunol. Cell. Biol.* 68:95–105 (1990) (Abstract).
Morland, C.M. et al., "A Simple Non–Isotopic Assay Discriminates Between Neutrophil and Eosinophil Adhesion to Endothelial Cells," *Am. Rev. Respir. Dis.* 141:A909 (1990).

Wegner, C.D. et al., "Intercellular Adhesion Molecule–1 (ICAM–1) in the Pathogenesis of Asthma," *Science* 247:456–459 (1990).
Kyan–Aung, U. et al., "Endothelial Leukocyte Adhesion Molecule–1 and Intercellular Adhesion Molecule–1 Mediate the Adhesion of Eosinophils to Endothelial Cells in Vitro and Are Expressed by Endothelium in Allergic Cutaneous Inflammation in Vivo," *J. Immunol.* 146:521–528 (1991).
Sherman–Gold, R., "Companies Pursue Therapies Based on Complex Cell Adhesion Molecules," *Genet. Eng. News* 13:6,7,14.
Osband, M.E. et al., "Problems in the Investigational Study and Clinical Use of Cancer Immunotherapy," *Immunol. Today* 11:193–195 (1990).
Jolliffe, L.K., "Humanized Antibodies: Enhancing Therapeutic Utility Through Antibody Engineering," Intern Rev. Immunol. 10:241–250 (1993).
Waldman, T.A., "Monoclonal Antibodies in Diagnosis and Therapy," *Science* 252:1657–1662 (1991).
Steiner, J. et al., "Phase II Clinical Trial Results—Too Many Expectations?," *Bio/Technol.* 11:644 (1993).
Shaffer, M., "Drug Giants, Start–Ups Target Adhesion Molecules, Key to Inflammatory Diseases," *Biotechnology Newswatch*, Oct. 4, 1993, p. 9.
Mountain, A. et al., "Engineering Antibodies for Therapy," *Biotech. Genet. Eng. Rev.* 10:1–13 (1992).
Edgington, S.M., "How Sweet It Is:Selectin–Mediating Drugs," *Bio/Technol.* 10:383–389 (1992).
Smith, C.W. et al., "Chemotactic Factors Regulate Lectin adhesion Molecule–1 (LECAM–1)–Dependent Neutrophil Adhesion to Cytokine–Stimulated Endothelial Cells in Vitro," *J. Clin. Invest.* 87:609–618 (1991).
Smith, C.W. et al., "Endothelial Adhesion Molecules and Their Role in Inflammation," *Canad, J. Physiol. Pharm.* 71:76–87 (1993).
Borrebaeck, C.A.K. et al., "Does Endogenous Glycosylation Prevent the Use of Mouse Monoclonal Antibodies as Cancer Therapeutics?," Immunol. Today 14:477–479 (1993).

*Primary Examiner*—Lila Feisee
*Assistant Examiner*—Phillip Gambel
*Attorney, Agent, or Firm*—Jeffrey I. Auerbach; Howrey & Simon

[57] ABSTRACT

A method for treating asthma in a patient using an agent selected from the group consisting of:

(a) an antibody capable of binding to ELAM-1;
(b) a fragment of the antibody (a), the fragment being capable of binding to ELAM-1;
(c) ELAM-1, being substantially free of natural contaminants;
(d) a functional derivative of ELAM-1;
(e) an antibody capable of binding to an ELAM-1 receptor;
(f) a fragment of the antibody (e), the fragment being capable of binding to an ELAM-1 receptor;
(g) an ELAM-1 receptor, being substantially free of natural contaminants; and .
(h) a functional derivative of an ELAM-1 receptor.

2 Claims, 4 Drawing Sheets

USE OF ENDOTHELIAL-LEUKOCYTE ADHESION MOLECULE-1 SPECIFIC ANTIBODIES IN THE TREATMENT OF ASTHMA

CROSS-REFERENCE TO RELATED APPLICATIONS

This application is a continuation of U.S. patent application Ser. No. 08/166,562 (filed Dec. 13, 1993) now abandoned, which is a continuation of U.S. patent application Ser. No. 07/738,633 (filed Jul. 31, 1991) now abandoned.

FIELD OF THE INVENTION

The present invention relates to the use of endothelial-leukocyte adhesion molecule-1 (ELAM-1), ligands thereto, and antibodies, in the treatment of asthma.

BACKGROUND OF THE INVENTION

ELAM-1 is an inducible endothelial cell surface glycoprotein. ELAM-1 is synthesized by endothelial cells in response to inflammatory agents and promotes adhesion of neutrophils, monocytes and a subpopulation of lymphocytes. The primary amino acid sequence of ELAM-1 suggests a complex domain structure containing a lectin-like amino terminus, an EGF-like domain and six consensus repeats similar to those found in complement regulatory proteins. Its expression is relatively restricted to activated vascular endothelium in vitro and in vivo. ELAM-1 is a member of a family of adhesion-receptor glycoproteins critical to interactions of circulating cells within the vasculature. This family has been designated the selectins or LEC-CAMS. The other selectins are LecCAM-1 AND CD62. Springer et al, Nature 349 (17): 196 (1991) and Bevilacqua et al, "Identification and Characterization of Endothelial-Leukocyte Adhesion Molecule-1", Chapter 16, *Leukocyte Adhesion Molecules* (T. A. Springer, D. C. Anderson, A. S. Rosenthal and R. Rothlein, Eds.) (Springer-Verlag New York Inc. 1990).

Asthma is a heterogenous family of diseases. It is characterized by a hyper responsiveness of the tracheobronchi to stimuli (McFadden, E. R. et al., In: *Harrison's Principles of Internal Medicine,* 10th Ed., Petersdorf, R. G. et al., Eds., McGraw-Hill, NY (1983), pages 1512–1519), Kay, A. B., *Allergy and Inflammation,* Academic Press, NY (1987); which references are incorporated herein by reference). Clinically, asthma is manifested by the extensive narrowing of the tracheobronchi, by thick tenacious secretions, by paroxysms of dyspnea, cough, and wheezing. Although the relative contribution of each of these conditions is unknown, the net result is an increase in airway resistance, hyperinflation of the lungs and thorax, abnormal distribution of ventilation and pulmonary blood flow. The disease is manifested in episodic periods of acute symptoms interspersed between symptom-free periods. The acute episodes result in hypoxia, and can be fatal. Approximately 3% of the general world population suffers from the disease.

Two types of asthma have been described: allergic asthma and idiosyncratic asthma. Allergic asthma is usually associated with a heritable allergic disease, such as rhinitis, urticaria, eczema, etc. The condition is characterized by positive wheal-and-flare reactions to intradermal injections of airborne antigens (such as pollen, environmental or occupational pollutants, etc.), and increased serum levels of IgE. The development of allergic asthma appears to be causally related to the presence of IgE antibodies in many patients. Asthma patients who do not exhibit the above described characteristics are considered to have idiosyncratic asthma.

Allergic asthma is believed to be dependent upon an IgE response controlled by T and B lymphocytes and activated by the interaction of airborne antigen with mast cell-bound pre-formed IgE molecules. The antigenic encounter must have occurred at concentrations sufficient to lead to IgE production for a prolonged period of time in order to sensitize an individual. Once sensitized, an asthma patient may exhibit symptoms in response to extremely low levels of antigen.

Asthma symptoms may be exacerbated by the presence and level of the triggering antigen, environmental factors, occupational factors, physical exertion, and emotional stress.

SUMMARY OF THE INVENTION

This invention relates to a method for treating asthma in a patient, which comprises administering to the patient a therapeutically effective amount of an agent selected from the group consisting of:

(a) an antibody capable of binding to ELAM-1;

(b) a fragment of the antibody (a), the fragment being capable of binding to ELAM-1;

(c) ELAM-1, being substantially free of natural contaminants;

(d) a functional derivative of ELAM-1;

(e) an antibody capable of binding to an ELAM-1 receptor;

(f) a fragment of the antibody (e), the fragment being capable of binding to an ELAM-1 receptor;

(g) an ELAM-1 receptor, being substantially free of natural contaminants; and (h) a functional derivative of an ELAM-1 receptor.

DESCRIPTION OF THE INVENTION

Figure 1:
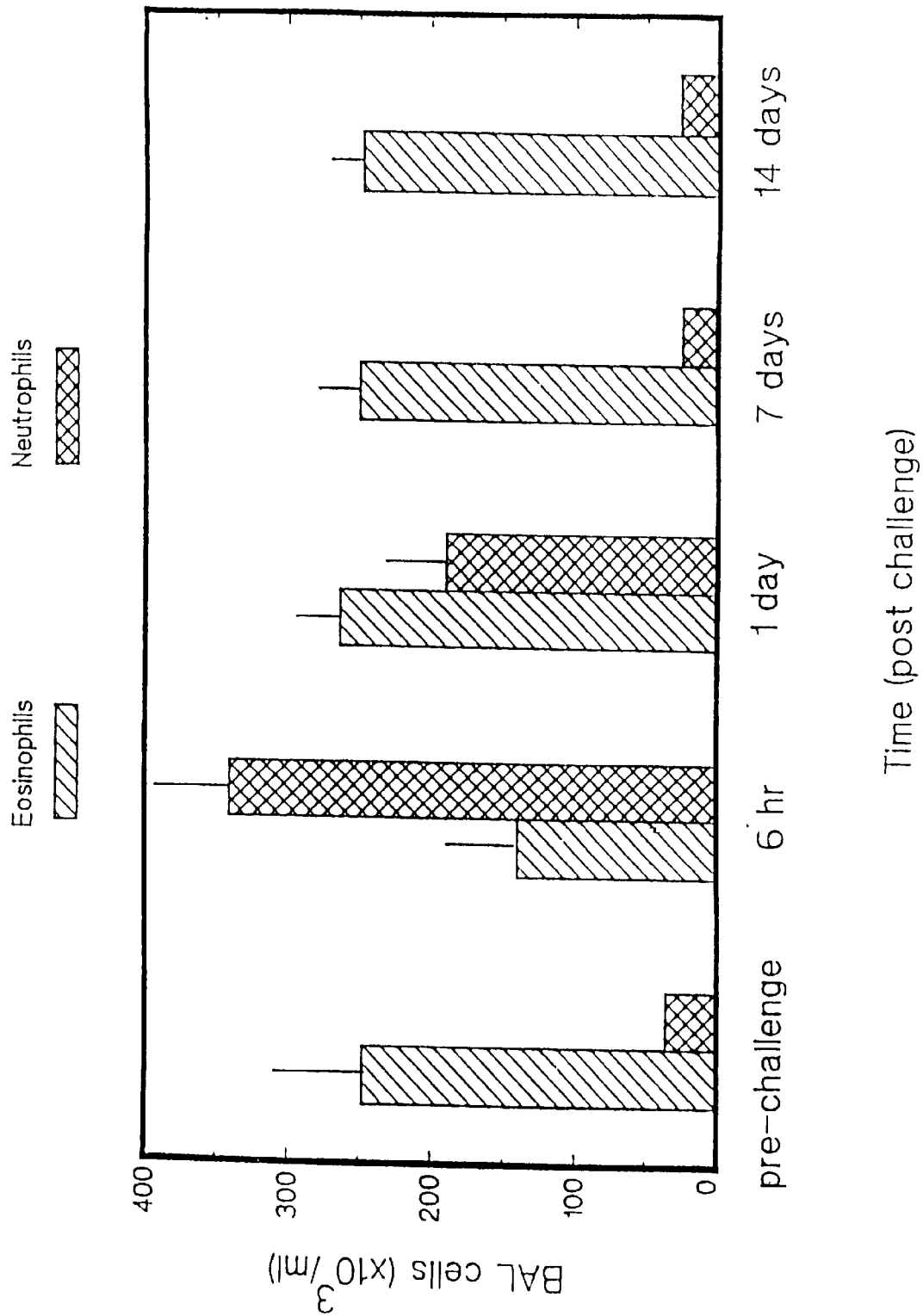
FIG. 1 shows airway cellular composition before and at several time points after antigen inhalation challenge. There was a large number of eosinophils recovered prior to antigen challenge. After challenge the number of eosinophils decreased but returned to prechallenge levels by day 1 and remained elevated at day 7 and 14. There was a striking influx of neutrophils associated with the late-phase bronchoconstriction response.

This invention relates to a method for treating asthma in a patient, which comprises administering to the patient a therapeutically effective amount of an agent selected from the group consisting of:

(a) an antibody capable of binding to ELAM-1;

(b) a fragment of the antibody (a), the fragment being capable of binding to ELAM-1;

(c) ELAM-1, being substantially free of natural contaminants;

(d) a functional derivative of ELAM-1;

(e) an antibody capable of binding to an ELAM-1 receptor;

(f) a fragment of the antibody (e), the fragment being capable of binding to an ELAM-1 receptor;

(g) an ELAM-1 receptor, being substantially free of natural contaminants; and (h) a functional derivative of an ELAM-1 receptor.

As used herein, "asthma" refers to either allergic or idiosyncratic asthma. An agent is said to have a therapeutic potential in the treatment of asthma if it may lessen (i.e., attentuate) the severity, extent or duration of the asthma symptoms. As used herein, an agent is said to be able to treat asthma if, when administered to a patient, the agent is capable of attentuating either the severity, extent or duration of the asthma symptoms.

One aspect of the present invention derives from the discovery that ELAM-1 contributes substantially to the development of antigen-induced airway inflammation.

ELAM-1 is a molecule expressed on the surface of endothelial cells that mediates adhesion of leukocytes to endothelial cells (Bevilacqua et al, Science 243: 1160 (1989), herein incorporated by reference).

An "ELAM-1 receptor", as used herein, is a molecule expressed on the surface of leukocytes that binds to ELAM-1 and is involved in ELAM-1-mediated binding to endothelial cells. This includes carbohydrate ligands of ELAM-1.

Another aspect of the present invention is the discovery that agents which prevent or inhibit neutrophil influx and binding to ELAM-1 on vascular endothelium may be employed in the treatment of asthma.

One example of agents which may be used in accordance with the present invention are ELAM-1 and functional derivatives of ELAM-1. Since ELAM-1 mediates adhesion of neutrophils to vascular endothelium by binding to a receptor molecule on the neutrophil cell surface, functional derivatives of ELAM-1 which can bind to the ELAM-1 receptor present on the neutrophils will compete with the ELAM-1 on lung endothelial cells, thus attentuating adhesion of the neutrophils, and providing a treatment for asthma.

A "functional derivative" of ELAM-1 is a compound which possesses a biological activity (either functional or structural) that is substantially similar to a biological activity of ELAM-1. The term "functional derivative" is intended to include the "fragments", "variants", or "chemical derivatives" of a molecule. A "fragment" of a molecule such as ELAM-1, is meant to refer to any polypeptide or carbohydrate subset of the molecule. Fragments of ELAM-1 which have ELAM-1 activity and which are soluble (i.e., not membrane bound) are especially preferred.

A "variant" of a molecule such as ELAM-1 is meant to refer to a molecule substantially similar in structure and function to either the entire molecule,,or to a fragment thereof. A molecule is said to be "substantially similar" to another molecule if both molecules have substantially similar structures or if both molecules possess a similar biological activity. A molecule is said to be a "chemical derivative" of another molecule when it contains additional chemical moieties not normally a part of the molecule. Such moieties may improve the molecule's solubility, absorption, biological half-life, etc.

An additional example of agents which may be used in accordance with the present invention to treat asthma are ELAM-1 receptors, or functional derivatives thereof. Such molecules and their functional derivatives can provide a treatment for asthma by virtue of their capacity to bind to the ELAM-1 of endothelial cells, and thus impair the ability of such cells to mediate binding and adhesion of leukocytes. Of special interest to the present invention are functional derivatives of ELAM-1 receptors which are soluble molecules. Examples of ELAM-1 receptors are the carbohydrate ligands of ELAM-1 on neutrophils such as sialylated lactosylceramides [see, e.g., Tiemeyer et al, Proc. Natl. Acad. Sci. USA 88: 1138 (1991)], or glycolipids or glycoproteins bearing the sialyl Lewis X antigen [see, e.g., Lowe et al, Cell 63: 475 (1990)].

ELAM-1 and ELAM-1 receptors are immunogenic molecules. Thus, it is possible to obtain antibodies capable of binding to ELAM-1 or an ELAM-1 receptor. Such antibodies may be used in accordance with the methods of the present invention in the treatment of asthma.

Such antibodies may be obtained by introducing either the purified molecules (or cells which naturally express these molecules) into an appropriate animal, as by intraperitoneal injection, etc. If desired, the serum of such an animal many be removed and used as a source of polyclonal antibodies capable of binding these molecules. It is, however, preferable to remove splenocytes from such animals, to fuse such spleen cells with a myeloma cell line and to permit such fusion cells to form a hybridoma cell which secretes monoclonal antibodies capable of binding ELAM-1.

The hybridoma cells, obtained in the manner described above may be screened as described above to identify desired hybridoma cells that secrete antibody capable of binding to ELAM-1 or to the ELAM-1 receptor.

Since such antibodies have the capacity to bind to ELAM-1 or to an ELAM-1 receptor, they (and their fragments having antigen binding ability, such as Fab, $F(ab)_2$, etc.) may be used to attenuate neutrophil adhesion, and thus provide an additional example of an agent which may be used in accordance with the present invention to treat asthma.

As indicated above, both polyclonal and monoclonal antibodies may be employed in accordance with the present invention. Of special interest to the present invention are antibodies to ELAM-1, which are produced in humans, or are "humanized" (i.e. non-immunogenic in a human) by recombinant or other technology. Humanized antibodies may be produced, for example by replacing an immunogenic portion of an antibody with a corresponding, but non-immunogenic portion (i.e. chimeric antibodies) (Robinson et al, International Patent Application 184,187; Taniguchi, M., European Patent Application 171,496; Morrison, S. L. et al, European Patent Application 173,494; Neuberger et al, PCT Application WO 86/01533; Cabilly et al, European Patent Application 125,023; Better et al, Science 240: 1041 (1988); Liu et al, Proc. Natl. Acad. Sci. USA 84: 3439 (1987); Liu et al, J.Immunol. 139: 3521 (1987); Sun et al, Proc. Natl. Acad. Sci. USA 84: 214 (1987); Nishimura et al, Canc. Res. 47: 999 (1987); Wood et al, Nature 314: 446 (1985)); Shaw et al, J. Natl. Cancer Inst. 80: 1553 (1988).

General reviews of "humanized" chimeric antibodies are provided by Morrison, S., Science 229: 1202 (1985) and by Oi et al, BioTechniques 4: 214 (1986).

Suitable "humanized" antibodies can be alternatively produced by CDR or CEA substitution (Jones et al, Nature 321: 552 (1986); Verhoeyan et al, Science 239: 1534 (1988); Beidler et al, J. Immunol. 141: 4053 (1988)).

The anti-asthma agents of the present invention may be obtained by natural processes (such as, for example, by inducing an animal, plant, fungi, bacteria, etc., to produce a non-immunoglobulin antagonists of ELAM-1, or by inducing an animal to produce polyclonal antibodies capable of binding to ELAM-1; by synthetic methods (such as, for example, by using the Merrifield method for synthesizing polypeptides to synthesize ELAM-1, functional derivatives of ELAM-1, or protein antagonists of ELAM-1 (either immunoglobulin or non-immunoglobulin)); by hybridoma technology (such as, for example, to produce monoclonal antibodies capable of binding to ELAM-1); or by recombinant technology (such as, for example, to produce the anti-asthma agents of the present invention in diverse hosts (i.e., yeast, bacteria, fungi, cultured mammalian cells, etc.) or from recombinant plasmids or viral vectors), or by proteolysis. The choice of which method to employ will depend upon factors such as convenience, desired yield, etc. It is not necessary to employ only one of the above described methods, processes, or technologies to produce a particular anti-asthma agent; the above described processes, methods, and technologies may be combined in order to obtain a particular anti-asthma agent.

Functional derivatives of ELAM-1, having up to about 100 residues may be conveniently prepared by in vitro synthesis. If desired, such fragments may be modified by reacting targeted amino acid residues of the purified or crude protein with an organic derivatizing agent that is capable of reacting with selected side chains or terminal residues. The resulting covalent derivatives may be used to identify residues important for biological activity.

The therapeutic effects of the anti-asthma agents of the present invention may be obtained by providing such agents to a patient by any suitable means (i.e. intravenously, intramuscularly, subcutaneously, enterally, or parenterally). It is preferred to administer the agents of the present invention intranasally as by nasal spray, swab, etc. It is especially preferred to administer such agents by oral inhalation, or via an oral spray or oral aerosol. When administering agents by injection, the administration may be by continuous infusion, or by single or multiple boluses.

The therapeutic advantages of any of the above discussed agents can be augmented through the use of functional derivatives possessing additional amino acid residues added to enhance coupling to carrier or to enhance the activity of the agent. The scope of the present invention is further intended to include functional derivatives of ELAM-1 which lack certain amino acid residues or which contain altered amino acid residues, so long as such derivatives exhibit the capacity to affect cellular adhesion.

The antibodies of the present invention, the ELAM-1 molecule and the ELAM-1 receptors, are said to be "substantially free of natural contaminants" if preparations which contain them are substantially free of materials with which these products are normally and naturally found.

The present invention extends to the use of antibodies, and biologically active fragments thereof, (whether polyclonal or monoclonal) which are capable of binding to ELAM-1 or to an ELAM-1 receptor, in the treatment of asthma.

In providing a patient with the anti-asthma agents of the present invention to a recipient patient, the dosage of administered agent will vary depending upon such factors as the patient's age, weight, height, sex, general medical condition, previous medical history, etc. In general, it is desirable to provide the recipient with a dosage of agent which is in the range of from about 1 pg/kg to 10 mg/kg (body weight of patient), although a lower or higher dosage may be administered. The therapeutically effective dose can be lowered by using combinations of the above described agents. As used herein, one compound is said to be additionally administered with a second compound when the administration of the two compounds is in such proximity of time that both compounds can be detected at the same time in the patient's serum.

The anti-asthma agents of the present invention are intended to be provided to recipient subjects in an amount sufficient to lessen or attenuate the severity, extent or duration of the asthma symptoms.

The antibody agents of the invention, or their fragments, may be administered either alone or in combination with one or more additional anti-asthma agents (such as methylxanthines (such as theophylline), beta-adrenergic agonists (such as catecholamines, resorcinols, saligenins, and ephedrine), glucocorticoids (such as hydrocortisone), chromones (such as cromolyn sodium) and anticholinergics (such as atropine), in order to decrease the amount of such agents needed to treat the asthma symptoms.

The administration of the agents of the invention may be for either a "prophylactic" or "therapeutic" purpose. When provided prophylactically, the agents are provided in advance of any asthma symptom. The prophylactic administration of the agents serves to prevent or attenuate any subsequent asthmatic response. When provided therapeutically, the agents are provided at (or shortly after) the onset of a symptom of asthma. The therapeutic administration of the agents serves to attenuate any actual asthmatic episode. The agents of the present invention may, thus, be provided either prior to the onset of an anticipated asthmatic episode (so as to attenuate the anticipated severity, duration or extent of the episode) of after the initiation of the episode.

A composition is said to be "pharmacologically acceptable" if its administration can be tolerated by a recipient patient. Such an agent is said to be administered in a "therapeutically effective amount" if the amount administered is physiologically significant. An agent is physiologically significant if its presence results in a detectable change in the physiology of a recipient patient.

The agents of the present invention can be formulated according to known methods to prepare pharmaceutically useful compositions, whereby these materials, or their functional derivatives, are combined in admixture with a pharmaceutically acceptable carrier vehicle. Suitable vehicles and their formulation, inclusive of other human proteins, e.g., human serum albumin, are described, for example, in Remington's Pharmaceutical Sciences (16th ed., Osol, A., Ed., Mack, Easton Pa. (1980)). In order to form a pharmaceutically acceptable compositions suitable for effective administration, such compositions will contain an effective amount of anti-ELAM-1 antibody or ELAM-1 molecule, or their functional derivatives, together with a suitable amount of carrier vehicle.

Additional pharmaceutical methods may be employed to control the duration of action. Control release preparationsxmay be achieved through the use of polymer to complex or absorb anti-ELAM-1 antibody or ELAM-1, or their functional derivatives. The controlled delivery may be exercised by selecting appropriate macromolecules (for example polyester, polyamino acids, polyvinyl, pyrrolidone, ethylenevinylacetate, methylcellulose, carboxymethylcellulose, or protamine, sulfate) and the concentration of macromolecules as well as the methods of incorporation in order to control release. Another possible method to control the duration of action by controlled release preparations is to incorporate anti-ELAM-1 antibody or ELAM-1 molecules, or their functional derivatives, into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, by coacervation techniques or by interfacial polymerization, for example, hydroxymethylcellulose or gelatine-microcapsules and poly(methylmethacylate) microcapsules, respectively, or in colloidal drug delivery systems, for example, liposomes, albumin microspheres, microemulsions, nanoparticles, and nanocapsules or in macroemulsions. Such techniques are disclosed in Remington's Pharmaceutical Sciences (1980).

Having now generally described the invention, the same will be more readily understood through reference to the following example which is provided by way of illustration, and is not intended to be limiting of the present invention, unless specified.

In the following example, the function of two vascular adhesion molecules, ICAM-1 and ELAM-1, in the development of antigen-induced acute airway inflammation and late-phase airway obstruction in primates, is described.

EXAMPLE 1

A. Materials and Methods

Animals: The animals used in this study were wild-caught adult male cynomolgus monkeys (Macaca fascicularis) weighing approximately 4 to 8 kg (Charles River Breeding Laboratories, Inc., Primate Imports, Port Washington, N.Y.). Each animal was housed individually in a specially designed open mesh cage and provided with food twice a day and water ad libitum.

Study Protocol: Each animal was anesthetized with an intramuscular injection of ketamine (4 mg/kg; Ketaset, Myoderm Medical Supply, Norristown, Pa.) and xylazine (1 mg/kg; Rompun, Miles Laboratories, Inc., Naperville, Ill.), intubated with a cuffed endotracheal tube and placed in the supine position. Ketamine (4 mg/kg, i.m.) was used as supplemental anesthesia as needed. Each animal then received a bolus intravenous injection of monoclonal antibody or vehicle (saline). Airway cellular composition was then evaluated by performing bronchoalveolar lavage (BAL) with a pediatric fiberoptic bronchoscope after which the animals were seated in the upright position in a specially designed support chair. Baseline respiratory system resistance (Rrs) was monitored for approximately 15 minutes followed by an inhaled antigen challenge (1 hr. post i.v. treatment). Rrs was monitored continuously for 1 hour after which the animals were allowed to recover from anesthesia and returned to their cages. At 4, 6, 8 and 10 hours after antigen inhalation and Rrs was monitored over a 15 minute time period to record the late-phase response. Cellular influx into the lungs during the peak late-phase response was assessed by performing BAL (opposite lung lavaged prior to antigen challenge).

The study was designed such that bracketing control experiments (vehicle treatment) were performed on each animal such that each animal served as its own control. Each study was separated by 14 days.

Monoclonal Antibody CL2: Antibody against ELAM-1 (CL2) was generated as described in Picker et al, Nature 349: 796 (1991). Stock CL2 solutions were diluted with saline (final concentration 2 mg/ml) immediately before intravenous injection into a peripheral leg vein. CL2 treatment was administered 1 hour before antigen inhalation challenge.

Rrs Measurements: Respiratory system impedance (Rrs) was measured by discrete frequency (4–40 Hz in 11 equal logarithmic steps) sinusoidal forced oscillations superimposed on tidal breathing as described in Wegner et al, *Respir. Physiol.* 55: 47 (1984). The mean of the real or inphase component of Zrs over the entire frequency range was then computed to provide a single value representation of Rrs.

Bronchoalveolar lavage (BAL): BAL was performed by guiding a fiberoptic bronchoscope (Olympus Optical, model 3C-10, Lake Success, N.Y.) past the carina and wedged into a $_5$th to $_7$th generation bronchus. A 15 ml aliquot of bicarbonate buffered saline (pH 7.4, 23° C.) was infused and gently aspirated through a channel in the bronchoscope. Collected samples were centrifuged at 2000 RPM for 10 minutes and the resulting cell pellets were resuspended in $Ca^{++}$ and $Mg^{++}$ free Hank's balanced salt solution. We have found previously that the BAL procedure will elicit a mild inflammatory response. Thus, to avoid the possible effects of BAL on lung cellular composition, BAL was performed alternating the right and left lungs before and after antigen challenge. The return volume of infused buffer was very constant throughout the study and the procedure was well tolerated by the animals. Total white cell counts were obtained using a Coulter counter (Coulter Electronics, model #10, Hialeah, Fla.).

Antigen Inhalation Challenge: Antigen inhalation challenges were administered by intermittent positive pressure breathing with a Bird Mard 7A respirator and micronebulizer (Bird Corporation, model #8158). Each challenge consisted of 15 breaths per minute (maximum inspiratory pressure of 20 $cmH_2O$) for 2 minutes. Ascaris summ extract (Greer Laboratories, Lenoir, N.C.) was diluted with phosphate buffered saline (PBS, pH 7.4) to the appropriate concentration for each animal (dose required to cause a 200–500% increase in Rrs during the immediate response). Antigen challenges were separated by 14 days for each animal. Each animal was fasted for 18 hours prior to the day of study.

Histochemistry: BAL cells were evaluated using cytocentrifuge preparations stained with Diff-Quick stain (Fisher Scientific, St. Louis, Mont.). Differential cell counts were determined by counting 200 cells and the percentage of each cell type was recorded.

Histology: Lung biopsy samples were obtained prior to antigen challenge and during the peak late-phase response with biopsy forceps and the fiberoptic bronchoscope. Immunohistochemical staining for identification of ELAM-1 on pulmonary vascular endothelium and airway epithelium was performed as described in Wegner et al, *Science* 247: 456 (1990).

Statistical Analysis: Data were analyzed statistically using two-way analysis of variance and Friedman's multiple range test.

B. Results

In the first series of experiments we examined the lung cellular composition, by BAL, before and at several time points after a single antigen challenge (FIG. 1). Prior to antigen challenge there were a large number of eosinophils recovered by BAL. At six hours post challenge (during the peak late-phase bronchoconstriction) the number of eosinophils decreased but returned to pre-challenge values by day 1. Eosinophils remained chronically elevated at days 7 and 14. Neutrophils, however, comprised a very small percentage of BAL cells before antigen challenge and were dramatically increased during the late-phase bronchoconstriction (6 hours). Neutrophils returned to basal levels by day 1 and remained low at days 7 and 14. The influx of neutrophils correlated significantly with the magnitude of the late-phase response ($r=-0.61$, $p<0.05$).

Figure 2A:
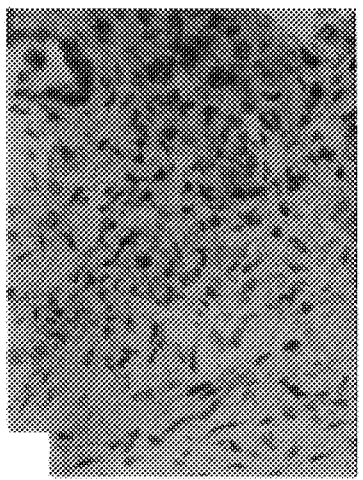
FIGS. 2A, 2B, and 2C show immunohistochemical staining with: (2A) normal mouse serum; (2B) antibody to ICAM-1; and (2C) antibody to ELAM-1, on lung tissue obtained by biopsy 6 hours post challenge. ICAM-1 staining was found on both airway epithelium and vascular endothelium. In contrast, staining for ELAM-1 was evident only on airway vascular endothelium.
Figure 2B:
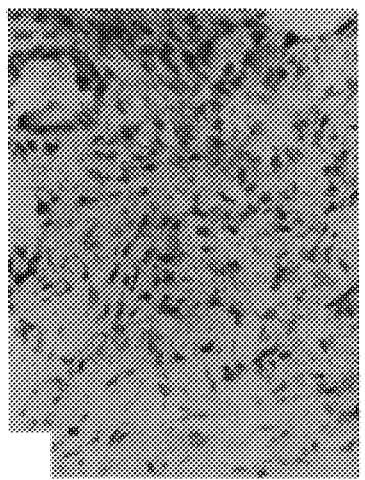
Figure 2C:
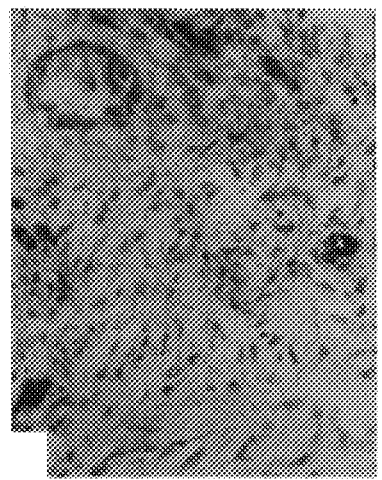

Immunohistochemical staining of lung tissue revealed positive staining for ICAM-1 on both pulmonary vascular endothelium and airway epithelium before antigen inhalation and at 6 hours after inhalation challenge (FIG. 2). In contrast, staining for ELAM-1 was not evident before antigen challenge but was dramatically increased on pulmonary vascular endothelium 6 hours post challenge. No staining for ELAM-1 was found on airway epithelium before or 6 hours post antigen challenge.

Figure 3:
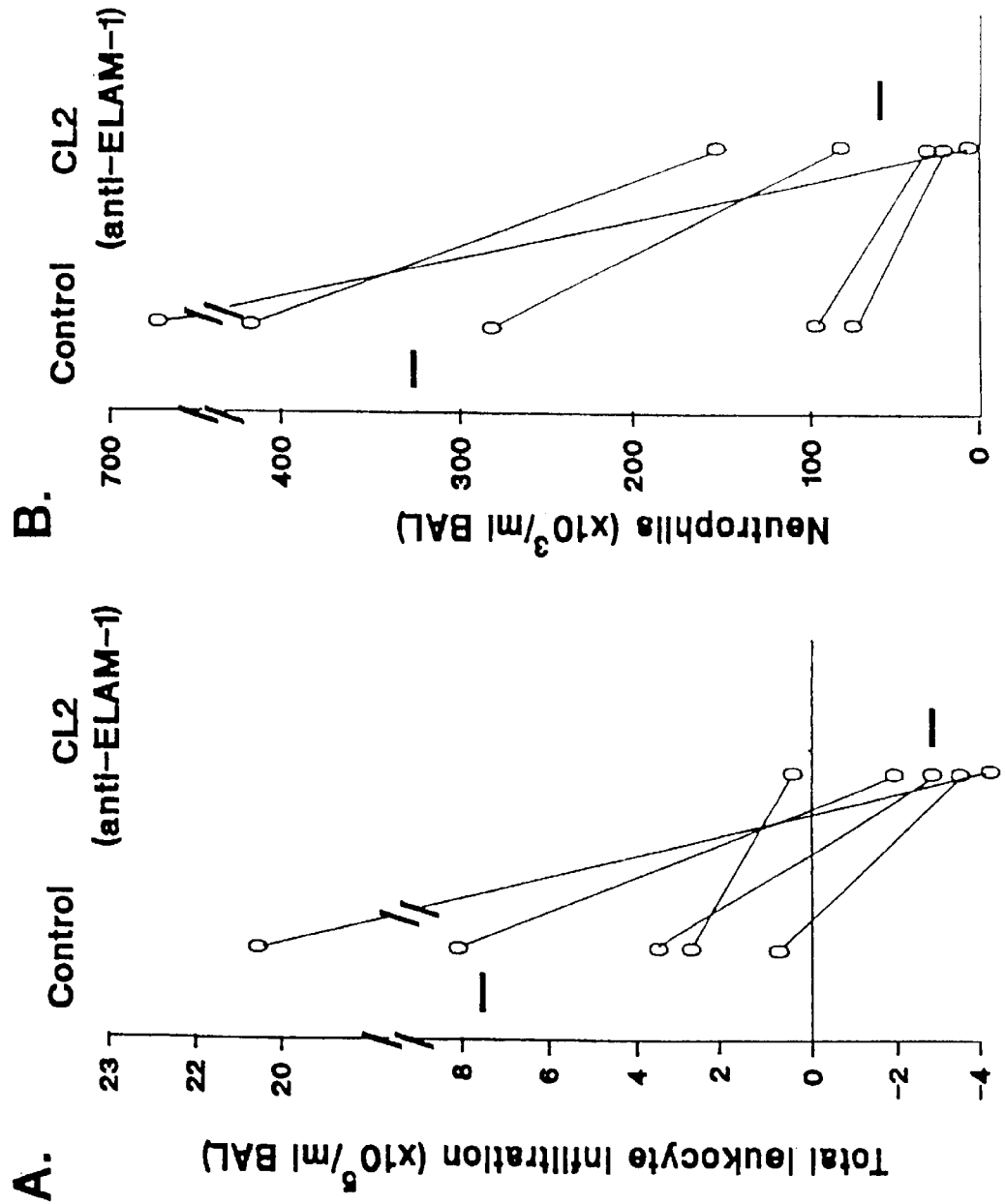
FIG. 3 shows the recovery of total leukocytes (A) and neutrophils (B) in control (vehicle treatment) animals and anti-ELAM-1 (CL2) treated animals. CL2 (2 mg/kg, i.v.) significantly attenuated the total number of leukocytes as well as the number of neutrophils infiltrating into the lungs 6 hours after antigen inhalation.
Figure 4:
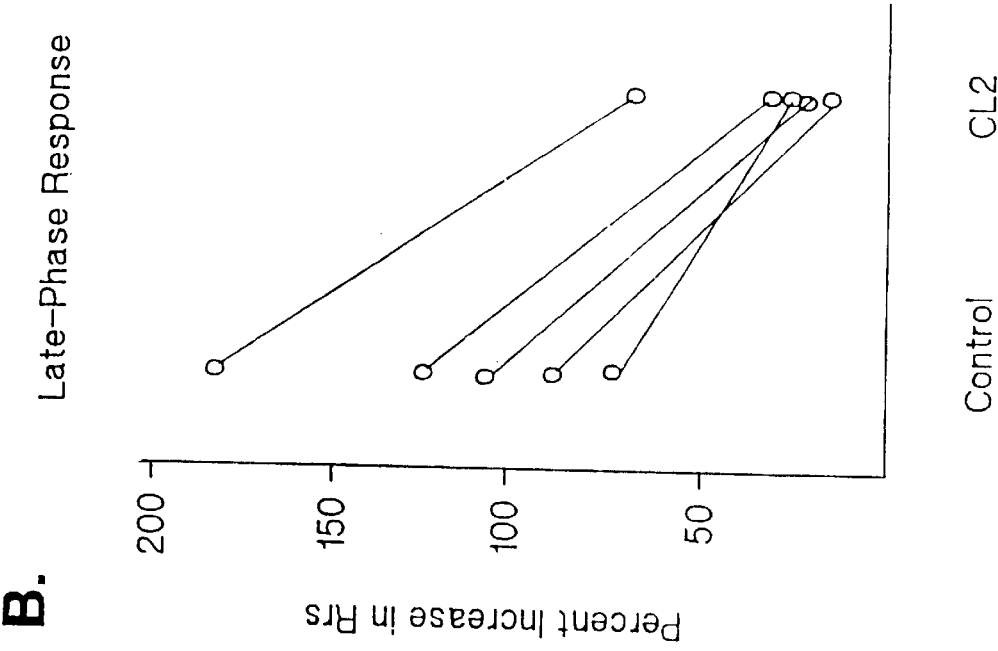
FIGS. 4A and 4B show the effects of anti-ELAM-1 (CL2) treatment on the immediate and late-phase response. CL2 significantly reduced the late-phase response but had no apparent effect on the immediate airway obstruction after antigen challenge.
Figure 4:
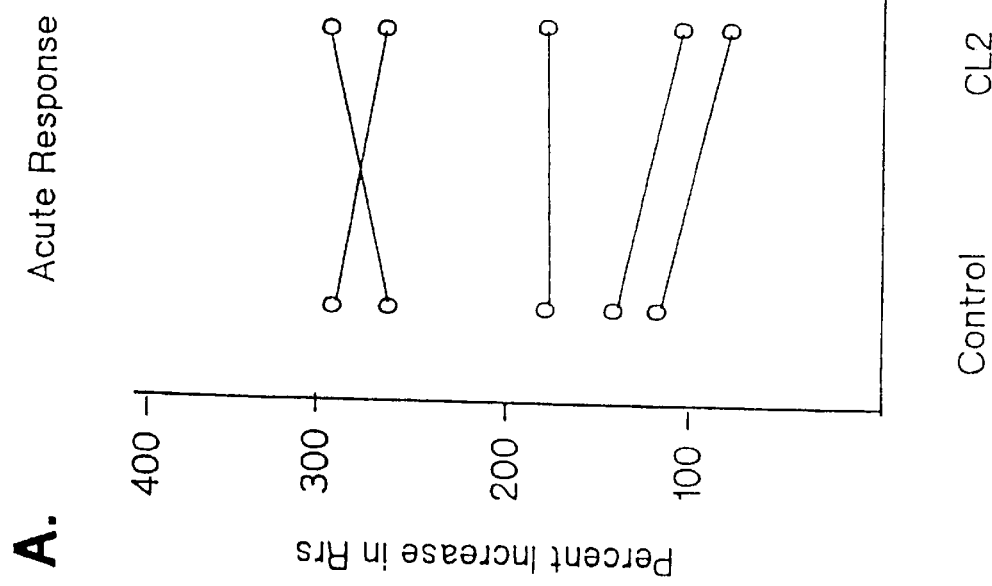

Pretreatment with anti-ELAM-1 (CL2) 1 hour before antigen inhalation significantly attenuated both the total leukocyte infiltration and the number of infiltrating neutrophils in all animals, markedly in 3 animals (FIG. 3). CL2 treatment resulted in a significant reduction in late-phase bronchoconstriction but had no apparent effect on the acute response. (FIG. 4).

What is claimed is:

1. A method for treating asthma in a patient which comprises administering to the patient an effective therapeutic amount of an antigen-binding antibody which specifically binds to ELAM-1 or an antigen-binding fragment thereof.

2. A method as recited in claim 1 wherein the antibody is a monoclonal antibody.

* * * * *

UNITED STATES PATENT AND TRADEMARK OFFICE
CERTIFICATE OF CORRECTION

| | | |
|---|---|---|
| PATENT NO. | : 5,843,441 | Page 1 of 1 |
| DATED | : December 1, 1998 | |
| INVENTOR(S) | : Robert H. Gundel, Craig D. Wegner, L. Gordon Letts and C. Wayne Smith | |

It is certified that error appears in the above-identified patent and that said Letters Patent is hereby corrected as shown below:

<u>Title page,</u>
Item [73], should read as follows:
-- [73] Assignee: Boehringer Ingelheim Pharmaceuticals, Inc., Ridgefield, Conn. and Baylor College of Medicine, Houston, Tex.

Signed and Sealed this

Eighteenth Day of June, 2002

*Attest:*

*Attesting Officer*

JAMES E. ROGAN
*Director of the United States Patent and Trademark Office*